United States Patent [19]

Kempa et al.

[11] Patent Number: 5,417,494
[45] Date of Patent: May 23, 1995

[54] CONTACTLESS TESTING OF ELECTRONIC MATERIALS AND DEVICES USING MICROWAVES

[75] Inventors: Krzysztof Kempa, Billerica; Roman Litovsky, Newton, both of Mass.

[73] Assignee: Exid, Inc., Billerica, Mass.

[21] Appl. No.: 877,468

[22] Filed: May 1, 1992

[51] Int. Cl.[6] .......................................... G01N 25/72
[52] U.S. Cl. .................................. 374/5; 219/711; 374/7; 374/124; 374/137; 356/237; 250/338.1
[58] Field of Search .................... 374/4, 5, 6, 7, 124, 374/137, 122, 161; 219/10.55 M, 10.55 B, 10.55 A; 356/237; 250/341, 338.1

[56] References Cited

U.S. PATENT DOCUMENTS

| | | | |
|---|---|---|---|
| 4,430,897 | 2/1984 | Quate | 374/5 |
| 4,468,136 | 8/1984 | Murphy et al. | 374/6 |
| 4,486,103 | 12/1984 | Ando | 374/4 |
| 4,521,118 | 6/1985 | Rosencwaig | 374/5 |
| 4,543,486 | 9/1985 | Rose | 374/4 |
| 4,640,626 | 2/1987 | Schmid et al. | 374/5 |
| 4,644,162 | 2/1987 | Bantel et al. | 374/5 |
| 4,854,724 | 8/1989 | Adams et al. | 374/5 |
| 4,965,451 | 10/1990 | Solter | 250/332 |
| 5,032,727 | 7/1991 | Cox, Jr. et al. | 374/5 |
| 5,047,713 | 9/1991 | Kirino et al. | 374/4 |
| 5,052,816 | 10/1991 | Nakamura et al. | 374/5 |

FOREIGN PATENT DOCUMENTS

| | | | |
|---|---|---|---|
| 0152419 | 11/1981 | Germany | 374/5 |
| 0098243 | 5/1987 | Japan | 374/4 |
| 2066482 | 7/1981 | United Kingdom | 374/4 |
| 0565239 | 7/1977 | U.S.S.R. | 374/5 |

OTHER PUBLICATIONS

Guy, Arthur W., "Analyses of Electromagnetic Fields Induced in Biological Tissues by Thermographic Studies on Equivalent Phantom Models", IEEE Trans. On Microwave Theory, vol. MTT-19, No. 2, Feb. 1971, pp. 205–214.
Lin, Lawrence H. et al., "High-Speed Inspection of LCD Panels", Insystems, San Jose, Calif., USA. (No Date).
Hall, Henry P. et al., "Testing TFT-LCD Substrates with a Transfer Admittance Method", SID 91 Digest, 1991, pp. 682–685.
Tse, P. K. et al., "Leakage Current and Current Distribution Investigation in High Voltage (320V) Integrated Circuits Using Fluorescent Microthermography", AT&T Bell Laboratories, (No Date).
Sega, Ronald M. et al., "Infrared Application to the Detection of Induced Surface Currents ", SPIE, vol. 304 Modern Utilization of Technology VII, 1981, pp. 84–91.

Primary Examiner—William A. Cuchlinski, Jr.
Assistant Examiner—Diego F. F. Gutierrez
Attorney, Agent, or Firm—Fish & Richardson

[57] ABSTRACT

A method and system for probing a volume of material by detecting local conductivity in the material using microwave radiation. The probed volume of material is exposed to microwave radiation of a wavelength selected to excite the carriers of electrical current and induce localized heating in regions of the volume of material which is an electronic material or a device. A thermographic imaging system detects size and distribution of the locally heated regions, and a processing system determines a selected property of the material by analyzing the size and distribution of the locally heated regions. The thermographic imaging system can be an infra-red imaging system which detects infra-red radiation emitted from the locally heated region, or it can be a system which deposits a thermally sensitive film onto a surface of the material and detects thermally induced changes in the deposited film caused by the transferred heat. The testing system can be also used in conjunction with a light source to probe distribution of photoexcited carriers, or with an electronic testing system to examine local conductivity and performance of devices in an active or passive state.

37 Claims, 5 Drawing Sheets

CONTACTLESS TESTING OF ELECTRONIC MATERIALS AND DEVICES USING MICROWAVES

BACKGROUND OF THE INVENTION

The invention relates to contactless non-destructive testing of electronic materials and devices.

In the process of fabrication of electronic devices, there is a need for non-destructive, contactless testing. This allows identification of technological defects in early production stages in order to either eliminate defective devices from further production, or to repair them, thereby increasing the production yield. Semiconductor and flat panel display (FPD) technologies are typical examples in which these concerns are important. In fabrication of semiconductor devices, semiconducting wafers are processed by lithography and doped by various atoms using numerous techniques, for example, ion implantation, in order to form regions of different carrier concentration buried in a wafer. In addition, the regions of different conductivity can be formed by controlled deposition of additional layers on the surface of a wafer. These layers are deposited by various deposition techniques including molecular beam epitaxy (MBE), chemical vapor deposition (CVD), thermal or electron beam evaporation, sputtering, and others. The processing steps that create regions of varying carrier concentration or mobility are performed at different stages of the fabrication process, and precise processing conditions, influenced by many factors, must be attained in order to obtain structures of required properties. These regions are utilized for fabrication of various electronic devices integrated on the wafer.

To increase the production yield and to minimize cost, a fraction of wafers is tested for deficiencies after each processing step, or set of steps, so that further processing of wafers that do not satisfy the required criteria is avoided. Typically, the testing is done by examining the wafers using optical or electron microscopy, or other optical methods. These tests, even though powerful, reveal predominantly the surface characteristics and, in general, can not reveal physical properties within the wafer. Other, usually destructive, tests are employed on a statistically selected number of devices or test structures present on the wafer. These tests can be time consuming and costly, and furthermore, frequently result in destruction of tested devices. Additionally, microelectronic devices are tested after their completion, but at this stage if a device does not satisfy the predetermined criteria due to a processing error, a whole batch of processed devices could be unusable.

In the FPD fabrication process, a set of thin, optically transparent conducting lines is deposited on insulating substrates (e.g. glass). Then, a liquid crystal material is placed between two such substrates forming an FPD. In this process, a number of defects (e.g., line discontinuities, interline short circuits, substrate surface inhomogeneities, line inhomogeneities, micro cracks) is inadvertently formed. It is extremely desirable to locate and repair these defects; thus there is a demand for a fast, nondestructive testing technique which can be applied to every FPD component after each technological step.

In summary, there is a need for contactless inspection of materials and devices at different stages of their fabrication. If the inspection results in early detection of structural defects or deviations from required characteristics, the production yield will significantly increase. Additionally, there is a need for a contactless inspection method which can examine uniformity and structural integrity of semiconducting or conducting layers of heterostructures created by MBE, CVD, evaporation, sputtering, plasma spraying, and other deposition techniques.

SUMMARY OF THE INVENTION

The invention tests materials non-destructively. It utilizes microwave excitation of electric current carriers and subsequent thermographic analysis to determine distribution of the excited carriers. This contactless inspection is performed by exposing the tested wafer to microwave radiation which induces electrical currents in regions where free carriers are present. The directional movement of free carriers causes localized heating which is proportional to the carrier concentration and carrier mobility. The locally heated regions of increased temperature emit infra-red radiation which is detected using an infra-red (IR) camera. The collected IR images are further processed to visualize the location and concentration of the carriers.

In one aspect, the invention is a system for probing a volume of material (e.g., electronic material or electronic device) by detecting local electrical conductivity in regions of the material using microwave induced localized heating. The system has a source of microwave radiation for exposing the volume of material with microwave radiation; the microwave radiation has a wavelength selected to excite carriers of electrical current and induce localized heating in regions of the volume of material. The system also has a thermographic imaging system for detecting size and distribution of the locally heated regions of the volume of material, where the size and distribution of the locally heated regions is dependent on local electrical conductivity in the material, and a processing unit adapted to determine selected property of the material by analyzing the detected size and distribution of the locally heated regions.

Preferred embodiments of this aspect of the invention may include a microwave cavity for containing the microwave radiation, a microwave coupling structure for coupling generated microwave radiation from the source to the volume of material, and a sample holder for orienting the volume of material relatively to an incoming beam of microwaves and into a line of sight of the detector. The microwave coupling structure is either a waveguide or an antenna system, both adapted to deliver the microwave radiation from the source of microwave radiation to the microwave cavity.

Preferred embodiments of this aspect of the invention may include a thermographic imaging system which has an infra-red detector for detecting the infra-red radiation emitted from the locally heated regions; intensity of the detected infra-red radiation is dependent on electrical conductivity within the locally heated regions. The imaging system also has a set of microscope lenses attached to the detector and adapted to magnify the infra-red image of the locally heated regions and to focus the image onto the infra-red detector, and a data processor for digitizing the detected image. The digitized image is assembled into pictures, and digitally manipulated to determine the size and distribution of the locally heated regions.

Preferred embodiments of this aspect of the invention may include a light source for generating free carriers within the volume of material. The distribution of these carriers is probed by the microwave radiation.

Preferred embodiments of this aspect of the invention may also include a configuration of electric contacts adapted to provide electric connections to surface regions of the volume of material, and an electric testing system connected to the probed material by the configuration of the electric contacts and adapted to electrically probe the volume of material while it is irradiated by the microwave radiation.

In another aspect of the invention, the thermographic imaging system has a system for depositing a thermally sensitive film onto a surface of the material, and a system for detecting thermally induced changes in regions of the deposited film caused by the transferred heat from the volume of material.

In preferred embodiments of this aspect of the invention, the system for detecting the thermally induced changes in regions of the deposited film may be an optical imaging system, an optical microscope system, an electron microscope system, a Raman spectrometer, an infra-red spectrometer, or an X-ray system; they all are adapted to detect the pattern of thermally induced changes of the thermally sensitive film.

The selected property of the material may be the structure of the material, its carrier distribution or the spatial distribution of a deposited conducting layer. The wavelength of the microwave radiation may be in the range of 1 GHz to 100 GHz. The volume of material may be semiconducting wafer with regions of different carrier distribution.

Other advantages and features of the invention will be apparent from the following description of the preferred embodiment and from the claims.

DESCRIPTION OF THE PREFERRED EMBODIMENTS

Figure 1:
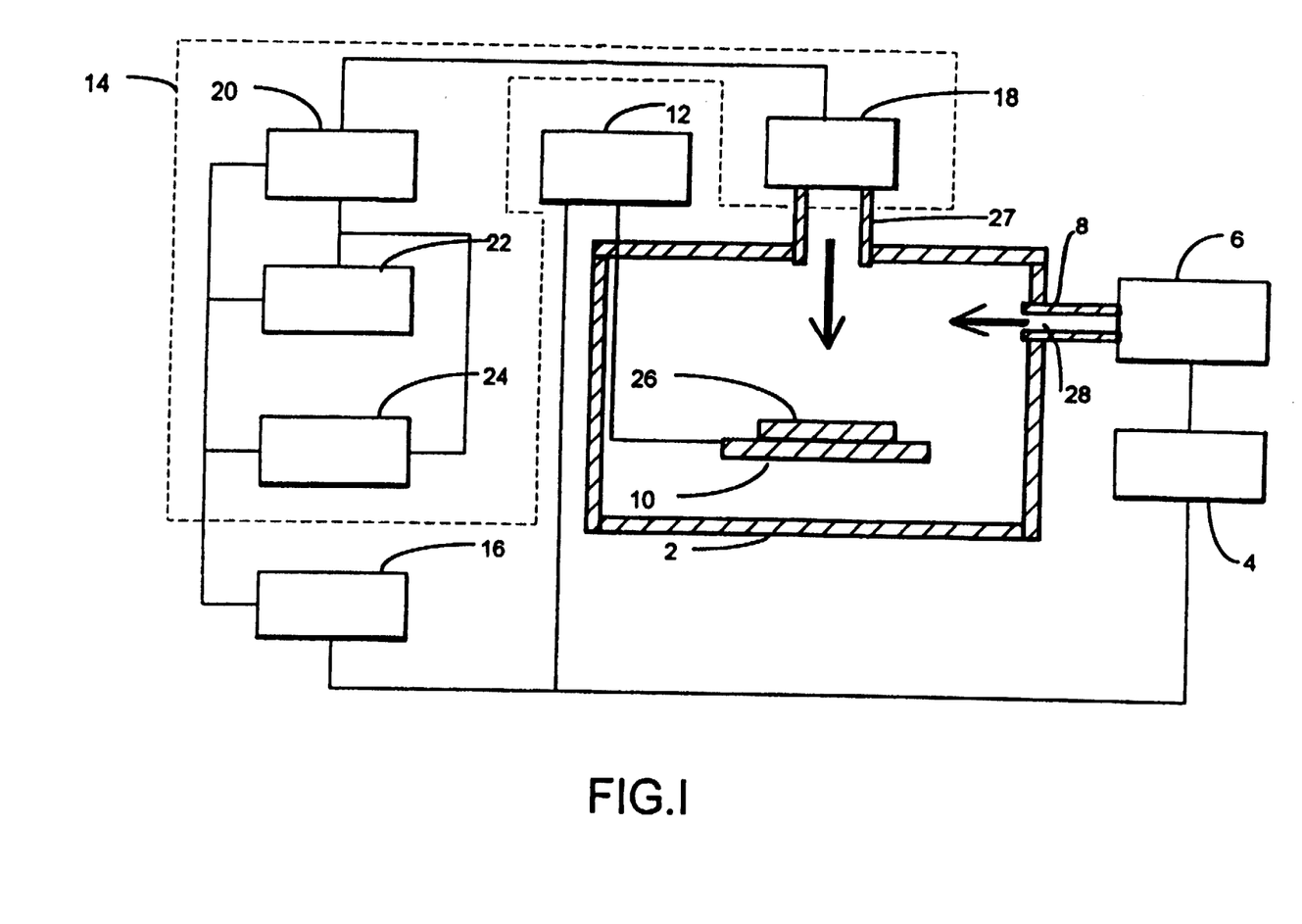
FIG. 1 is a diagrammatic view of a contactless testing system embodying the invention wherein the thermographic imaging unit is an infra-red camera.

Referring to FIG. 1, a contactless testing system has a shielded microwave cavity 2, a microwave power supply 4, a source of microwave radiation 6, a wave guide 8, a sample holder 10, an xyz sample position control 12, a thermographic imaging system 14, and a process control 16. Thermographic imaging system 14 consists of an infra-red (IR) camera 18, a data processor 20, a monitor 22, and a printer 24. A sample 26 is located on sample holder 10 and its movement is controlled by xyz control 12. IR camera 18 is attached to a port 27 and rectangular wave guide 8 is attached to a port 28. Port 28 is constructed to enable introduction of radiation into microwave cavity 2 via waveguide 8, and port 27 enables observation of sample 26 by IR camera 18. IR camera 18 detects radiation in the range of 3 to 12 $\mu$m. In one embodiment, thermographic imaging system 14 is the infra-red imaging system Inframetrics 760 (produced by Inframetrics Inc. of Billerica, Mass.), and microwave radiation source 6 is a magnetron which generates microwave radiation of 2.45 GHz.

Sample holder 10 is made of a non-absorbing material, for example, glass or Teflon ® and can be cooled by water or liquid nitrogen circulating in a set of tubing embedded in the sample holder; this partially eliminates thermal background noise. Source of microwave radiation 6 (for example, a klystron, magnetron, semiconductor diode, RF transistor, or other oscillator) is powered by a DC or RF power supply 4 controlled by process control 16. The system uses microwave radiation in the range of 1 GHz to 100 GHz.

In the testing process, a sample is loaded onto sample holder 10 through a loading port, not shown in FIG. 1, into microwave cavity 2. Sample holder 10 is positioned under port 27 wherein the movement of sample holder 10 is controlled by xyz position control 12 actuated by process control 16. Subsequently, the whole sample (e.g., a processed semiconducting wafer with regions of different carrier concentration, a dielectric with conducting surface regions, or a metal with insulating surface regions) is uniformly irradiated by microwave radiation generated by microwave source 6. The microwave radiation is transmitted via rectangular waveguide 8 to microwave cavity 2 and enters the cavity through port 28. The microwave radiation induces local electrical currents which cause localized Joule heating proportional to the carrier concentration and the carrier mobility. Concurrently, IR radiation is emitted from the locally heated regions of sample 26 and detected by IR camera 18 of thermographic imaging system 14. The infrared signal detected by IR camera 18 is digitized and processed by a data processor 20. A picture created from the digitized signal is displayed on monitor 22 and printed on printer 24. Process control 16 governs the entire action of the testing system.

The IR camera has a set of microscope lenses for achieving the desired magnification of the detected infra-red image. In order to inspect small features on large samples, for example, on wafers of 12" diameter, or 10" flat panel display, IR camera 18 systematically scans the surface of the sample, dwells in each subsequent position while collecting the IR signal from that pixel. The detected signal is digitized by data processor 20 and the digitized image is stored in the memory of process control 16. The pixel size varies depending on the magnification of the selected lens of the microscope system.

The spatial resolution of the testing system is limited by the sensitivity of the IR camera to the wavelength of the IR radiation carrying the image. IR camera 18 detects IR radiation in the range of 3 to 12 $\mu$m. Therefore, the resolution of the system is about 12 $\mu$m. However, if an IR camera sensitive to the radiation in the range of 3 to 5 $\mu$m is used, the resolution of the system will improve to about 5 $\mu$m. Thermal sensitivity of a commercially available IR camera is about 0.1 degree. The system can detect carrier concentration as low as $10^{14}$ cm$^{-3}$ using about 100 W of radiation.

To perform automatic evaluation of the sample quality, the collected images are processed by process control 16 and compared to a template image stored in the memory of process control 16. This test can be conducted on a production line or in a laboratory; the evaluation can be executed automatically or manually. To perform manual evaluation of the sample, process control 16 sends the processed image to monitor 22 and to printer 24 for evaluation by a system operator. The power of the microwave radiation is automatically adjusted to keep the sample in a steady state condition for the duration of the scan. Several subsequent scans can be taken to image the diffusion of heat from the heated regions of increased carrier concentration. Observation of the heat diffusion provides additional structural information about the sample.

In another mode of operation, IR camera 18 remains stationary and operates in coordination with the scanning movement of sample holder 10 which enables the inspection of the entire surface of the sample. This process is again managed by process control 16.

Figure 2:
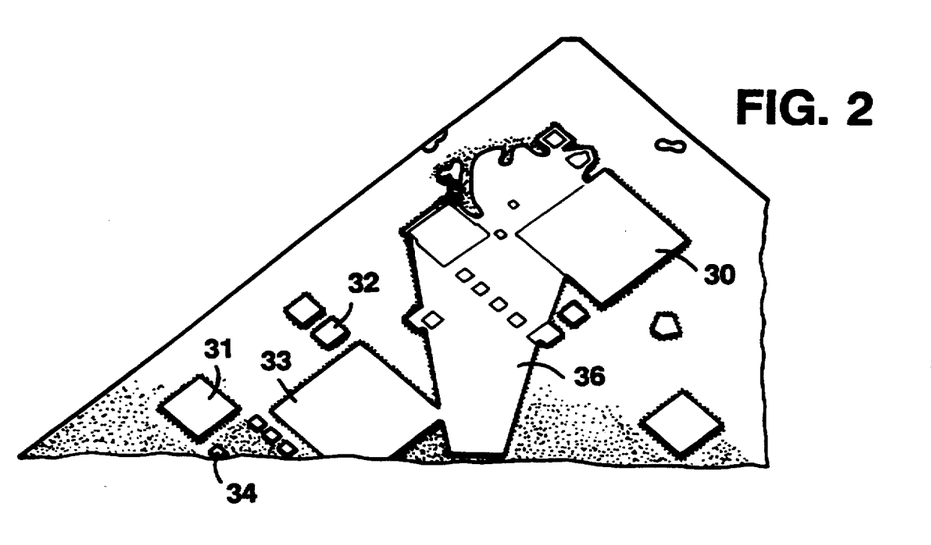
FIG. 2 is a thermal image of a microwave irradiated Si wafer visualizing regions of different donor density.

FIG. 2 shows an infra-red image of a Si wafer with regions of diffused carriers. The bulk acceptor density of the wafer is $10^{14}$ cm$^{-3}$. Regions 30, 31, 32, 33 and 34 are doped regions of different size and different donor densities. The IR picture visualizes these regions, wherein the size of the largest region 30 is 5 mm × 5 mm. The irregularly shaped region 36 near the center of the picture is an accidentally diffused metallic contamination. In a fabrication process, if a contamination region is detected, the wafer is excluded from additional processing. Similarly as for the contaminated region, a crack in the wafer or other structural inhomogeneity can be detected if the inhomogeneity has different carrier mobility than the bulk wafer.

Absorption of microwaves can be modified by selecting a suitable microwave frequency. At lower microwave frequencies the coupling of microwaves to the sample can be improved by using a microwave antenna system with one end closely positioned to the sample. At higher frequencies it is preferable to use a waveguide.

Figure 3:
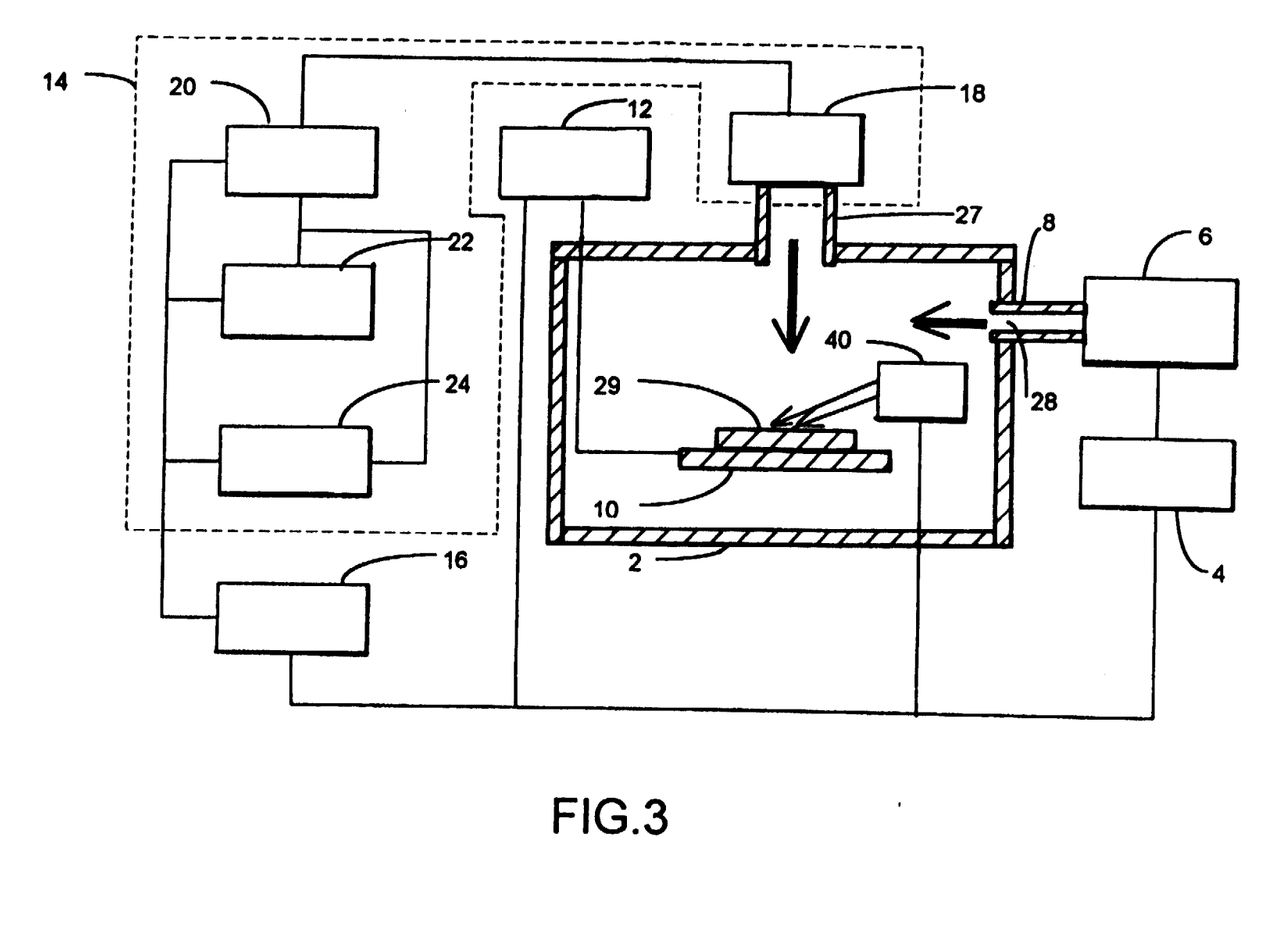
FIG. 3 is a diagrammatic view of the contactless testing system of FIG. 1 further including a light source for probing the concentration and location of photoinduced carriers.
Figure 4:
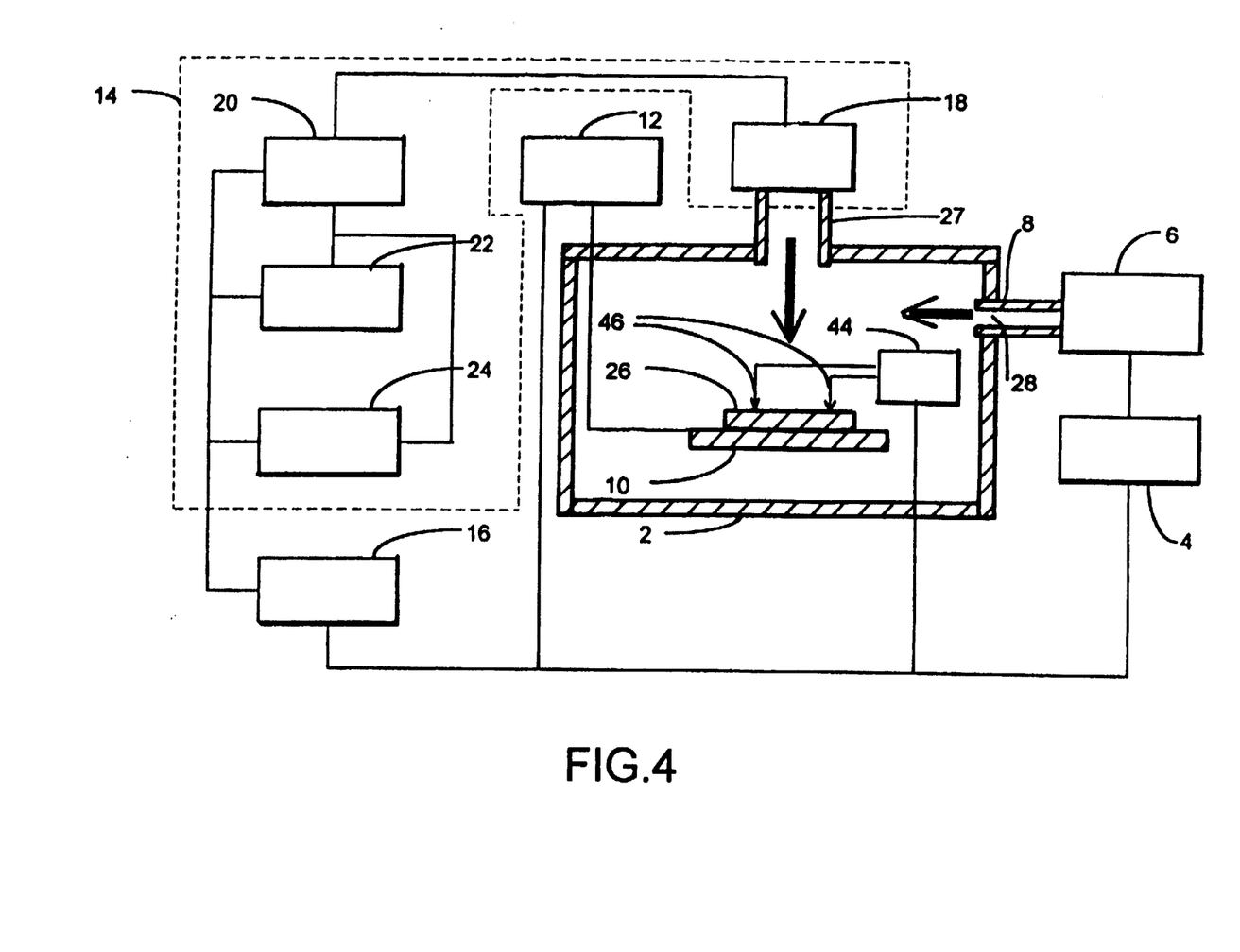
FIG. 4 is a diagrammatic view of the contactless testing system of FIG. 1 further including a configuration of electric probe tips connecting the tested material to an electronic testing system.
Figure 5:
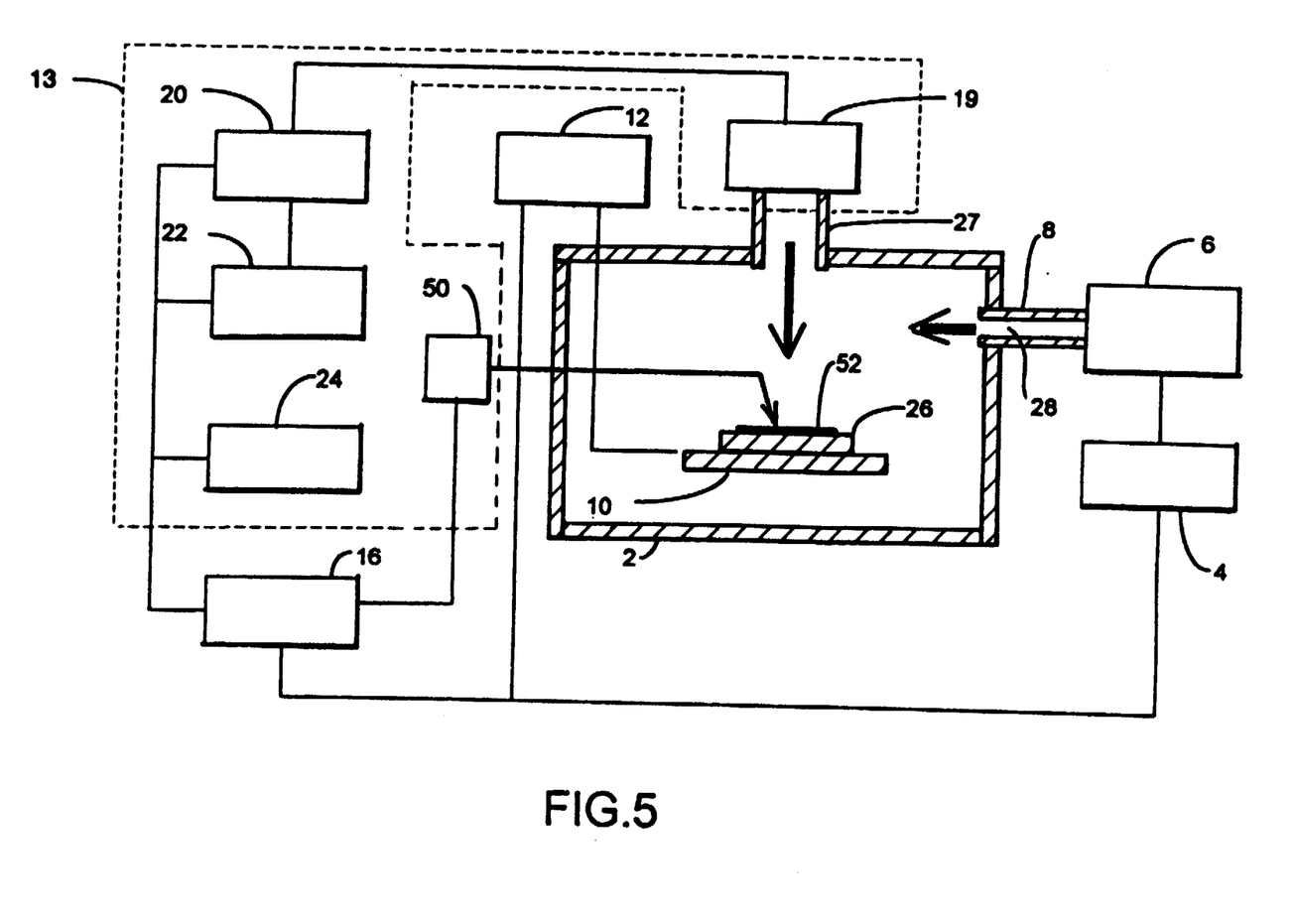
FIG. 5 is a diagrammatic view of a contactless testing system embodying the invention wherein the thermographic imaging is performed using a thermally sensitive thin film deposited on the probed sample.

The microwave source can operate in a continuous mode or in a pulse mode. The continuous mode is used simultaneously with the scanning action of IR camera 18; the probed sample is in a steady state. The design of the system of FIG. 1 enables simultaneous operation without substantial interference. On the other hand, the pulse mode is used to examine transient effects, or is used in conjunction with other testing systems, as shown in FIGS. 3, 4 and 5.

In general, the system can be used to examine structure, homogeneity, topology, and technological imperfections of samples with regions of different concentration or mobility of electric current carriers. The samples are semiconducting wafers with integrated circuits fabricated on them, biomolecular films, printed circuit boards, or any other material consisting of conducting and nonconducting regions or layers. However, large areas of high conductivity are difficult to probe since the microwave radiation is reflected from the metallic surface, and also the excited currents cause inherently low Joule heating. Other samples are dielectric panels with conducting lines deposited on the surface used in fabrication of flat panel displays, also called liquid crystal displays. The testing system detects imperfections in the shape and homogeneity of these conducting lines.

Many testing procedures require uniform irradiation of the tested sample to obtain uniform heating. The uniform irradiation is achieved using a resonant microwave cavity with mechanical or electrical stirring of modes, or applying rotation. If nonresonant cavities are used, uniform irradiation is achieved using multiple sources (e.g., using a multislot array antenna).

In another embodiment, polarized microwave radiation is used to probe samples with motion of carriers restricted to zero, one or two dimensions. These samples with carriers confined to quantum wells, quantum wires, or quantum dots are frequently used in microelectronics and fabricated by sequentially depositing layers of different materials capable of epitaxial growth. Referring to FIG. 1, source 6 generates polarized microwave radiation which induces preferentially oriented currents causing anisotropic heating that is detected by the thermographic imaging system. By rotating the probed sample, three dimensional thermal images are created.

In another embodiment, the system of FIG. 1 is used in cooperation with a light source generating free carriers, electric current externally applied to the sample, or externally applied electromagnetic field. These techniques are capable to examine samples in a passive or active state. In an active state, functionality of a device is tested electronically; thus, this testing technique requires to have electric leads or probe tips attached to the device. The pulsed or continuous microwave radiation irradiates the device, which is also subjected to external currents and voltages from an outside source. In this regime, both external electric currents and microwave induced currents cause heating which produces IR radiation emitted from the heated regions. The IR radiation is again detected by the thermographic imaging system.

Referring to FIG. 3, the system of FIG. 1 is further equipped with a light source 40 connected to process control 16. The system is used to probe the concentration and location of photoinduced carriers. A semiconducting sample 29 is first irradiated by light of suitable wavelength generated by light source 40. The absorbed photons generate free electron hole pairs. Subsequently, the microwave radiation, generated by source 6 operating in a pulse mode, irradiates the sample and induces localized Joule heating within the sample. The emitted IR radiation is detected by thermographic imaging system 14. The whole process is again controlled by process control 16.

Referring to FIG. 4, the system of FIG. 1 is further equipped with an electric testing system 44 connected to tested sample 26 by electric contacts 46. Electric testing system 44 (e.g., a current source, voltage source, amperemeter, voltmeter, lock-in amplifier) electrically tests sample 26. In addition, microwave source 6 generates continuous or pulsed radiation which induces localized currents in the tested sample, as previously described. Thermographic imaging system 14 detects heat generated by both external electrical sources and microwave radiation. Process control 16 governs the whole testing procedures and automatically evaluates the results using predetermined schemes.

In another embodiment, referring to FIG. 5, a different type of thermographic imaging is used. A thermographic imaging system 13 has a deposition system 50, a camera 19, data processor 20, monitor 22, and printer 24. Deposition system 50 deposits a thin, thermally sensitive film 52 on the surface of sample 26 before the sample is exposed to microwave radiation. Source of microwave radiation 6 irradiates sample 26 and induces localized heating in the sample. Deposition system 42 deposits a thin layer of film 52 on the sample surface. The heat transferred from the sample modifies film 52 and forms a pattern in film 52 which mimics the pattern of the locally heated regions of the sample. The film modifications are manifested as changes in physical properties of the film, for example, structure, color, stress, or luminescence and are registered by a number of different techniques. The embodiment of FIG. 5 uses optical methods to examine the thermally induced modifications. Camera 18 with a microscope lens system is used to detect the pattern of the film. Similarly as in the embodiments of FIGS. 1, 2 and 4, the imaging system scans the whole film surface, and saves the film images in the memory of data processor 20. To increase the system resolution, ultraviolet radiation can be used to image film 52. The spatial resolution is also limited by the pattern quality of film 52. In other embodiments of FIG. 5, other than optical methods are used to examine the thermally induced modifications of film 52, e.g., camera 19 can be replaced by a Raman spectrometer, an infra-red spectrometer, a spectrophotometer, or an X-ray system to observe film 52.

What is claimed is:

1. A method of probing a volume of material by detecting local electrical conductivity in regions of said material using microwave excited currents that induce localized heating, said method comprising the steps of:
   exposing said volume of material with microwave radiation of a wavelength selected to excite carriers of electrical current thereby inducing localized heating in regions of said volume of material,
   detecting size and distribution of said locally heated regions of said volume of material, said size and distribution of said locally heated regions being dependent on local electrical conductivity in said material, and
   determining selected property of said material by analyzing said detected size and distribution of said locally heated regions.

2. The method of claim 1 wherein said wavelength of said microwave radiation is in the range of 1 GHz to 100 GHz.

3. The method of claim 1 wherein said step of detecting size and distribution of locally heated regions comprises
   detecting infra-red radiation emitted from said locally heated regions using an infra-red imaging system, intensity of said detected infra-red radiation being dependent on said electrical conductivity in said locally heated regions.

4. The method of claim 3 further comprising the steps of:
   attaching electric contacts to surface regions of said volume of material, and
   electrically testing said material by applying external electrical source while irradiating said material by said microwave radiation.

5. The method of claim 3 further comprising the steps of:
   irradiating said volume of material with light of a wavelength selected to create free carriers in said material, and
   determining distribution of said free carriers in said material.

6. The method of claim 3, 4 or 5 further comprising applying electromagnetic field to said volume of material.

7. The method of claim 1 wherein said step of detecting size and distribution of locally heated regions comprises
   depositing a thermally sensitive film onto a surface of said material, and
   detecting thermally induced changes in regions of said deposited film caused by transferred heat from said volume of material.

8. The method of claim 3 or 7 wherein said selected property is carrier distribution.

9. The method of claim 3 or 7 wherein said selected property is the structure of said material.

10. The method of claim 3 or 7 wherein said selected property is spatial distribution of a deposited conducting layer.

11. The method of claim 7 wherein said step of detecting said thermally induced changes is performed utilizing an optical imaging system.

12. The method of claim 7 wherein said step of detecting said thermally induced changes is performed utilizing an optical microscope system.

13. The method of claim 7 wherein said step of detecting said thermally induced changes is performed utilizing an electron microscope system.

14. The method of claim 7 wherein said step of detecting said thermally induced changes is performed utilizing a Raman spectrometer.

15. The method of claim 7 wherein said step of detecting said thermally induced changes is performed utilizing an infra-red spectrometer.

16. The method of claim 7 wherein said step of detecting said thermally induced changes s performed utilizing an X-ray system.

17. The method of claim 3 or 7 wherein said volume of material is a semiconducting wafer with regions of different carrier distribution.

18. A system for probing a volume of material by detecting local electrical conductivity in regions of said material using microwave excited currents that induce localized heating, said system comprising
   a source of microwave radiation for exposing said volume of material with microwave radiation, said microwave radiation having a wavelength selected to excite carriers of electrical current thereby inducing localized heating in regions of said volume of material,
   a thermographic imaging system for detecting size and distribution of said locally heated regions of said volume of material, said size and distribution of said locally heated regions being dependent on local electrical conductivity in said material, and
   processing means adapted to determine selected property of said material by analyzing said detected size and distribution of said locally heated regions.

19. The system of claim 18 wherein said wavelength of said microwave radiation is in the range of 1 GHz to 100 GHz.

20. The system of claim 18 wherein said thermographic imaging system comprises
   an infra-red detector for detecting infra-red radiation emitted from said locally heated regions, the intensity of said detected infra-red radiation being dependent on said electrical conductivity in said locally heated regions, a set of microscope lenses attached to said detector and adapted to magnify a detected infra-red image of locally heated regions and to focus said image onto said infra-red detector, and a data processor for digitizing said image, assembling said image into pictures, and digitally manipulating said image to determine said size and distribution of said locally heated regions.

21. The system of claim 20 further comprising a microwave cavity for containing said microwave radiation, a microwave coupling means for coupling said microwave radiation from said source to said volume of material, and positioning means for orienting said volume of material relatively to said microwave radiation and into a line of sight of said thermographic imaging system.

22. The system of claim 21 wherein said microwave coupling means is a waveguide for delivering said microwave radiation from said source of microwave radiation to said microwave cavity.

23. The system of claim 21 wherein said microwave coupling means is an antenna system for delivering said microwave radiation from said source of microwave radiation to said material.

24. The system of claim 20 further comprising a light source for irradiating said volume of material with light of a wavelength selected to create free carriers in said material, wherein distribution of said free carriers is probed by said microwave radiation.

25. The system of claim 20 further comprising electric contacting means for providing electric connections to surface regions of said volume of material, and an electric testing means connected to said probed material by said electric contacting means and adapted to electrically probe said volume of material while irradiating said material by said microwave radiation.

26. The system of claim 24 or 25 further comprising means for applying electromagnetic field to said volume of material.

27. The system of claim 18 wherein said thermographic imaging system comprises a system for depositing a thermally sensitive film onto a surface of said material, a system for detecting thermally induced changes in regions of said deposited thermally sensitive film caused by the transferred heat from said volume of material, and processing means adapted to interpret said detected thermally induced changes to determine said size and distribution of said locally heated regions.

28. The system of claim 20 or 27 wherein said selected property is carrier distribution.

29. The system of claim 20 or 27 wherein said selected property is the structure of said material.

30. The system of claim 20 or 27 wherein said selected property is spatial distribution of a deposited conducting layer.

31. The system of claim 27 wherein said system for detecting thermally induced changes is an optical imaging system.

32. The system of claim 27 wherein said system for detecting thermally induced changes is an optical microscope system.

33. The system of claim 27 wherein said system for detecting thermally induced changes is an electron microscope system.

34. The system of claim 27 wherein said system for detecting thermally induced changes is a Raman spectrometer.

35. The system of claim 27 wherein said system for detecting thermally induced changes is an infra-red spectrometer.

36. The system of claim 27 wherein said system for detecting thermally induced changes is an X-ray system.

37. The system of claim 20 or 27 wherein said volume of material is a semiconducting wafer with regions of different carrier distribution.

* * * * *